US00PP24408P3

(12) United States Plant Patent
White

(10) Patent No.: US PP24,408 P3
(45) Date of Patent: Apr. 29, 2014

(54) PEAR TREE NAMED 'PREMP109'

(50) Latin Name: *Pyrus pyrifolia×Bretschneideri*
Varietal Denomination: PremP109

(75) Inventor: Allan White, Havelock North (NZ)

(73) Assignee: Prevar Limited, Hastings (NZ)

( * ) Notice: Subject to any disclaimer, the term of this patent is extended or adjusted under 35 U.S.C. 154(b) by 100 days.

(21) Appl. No.: 13/374,755

(22) Filed: Jan. 10, 2012

(65) Prior Publication Data

US 2012/0185978 P1 Jul. 19, 2012

Related U.S. Application Data

(60) Provisional application No. 61/461,521, filed on Jan. 18, 2011.

(51) Int. Cl.
*A01H 5/00* (2006.01)

(52) U.S. Cl.
USPC ..... Plt./178; Plt./176

(58) Field of Classification Search
USPC ..... Plt./176, 178
See application file for complete search history.

*Primary Examiner* — Susan McCormick Ewoldt
(74) *Attorney, Agent, or Firm* — Ballew Law

(57) ABSTRACT

A new and distinct pear tree named 'PremP109' is disclosed. The new pear is notable for its attractive appearance, superb texture, improved flavor and long shelf life.

2 Drawing Sheets

Latin name of the genus and species of the plant claimed: *Pyrus pyrifolia×Bretschneideri*.

Variety denomination: 'PREMP109'.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT-DISC

Not Applicable

BRIEF DESCRIPTION OF THE PHOTOGRAPHS

Figure 1:
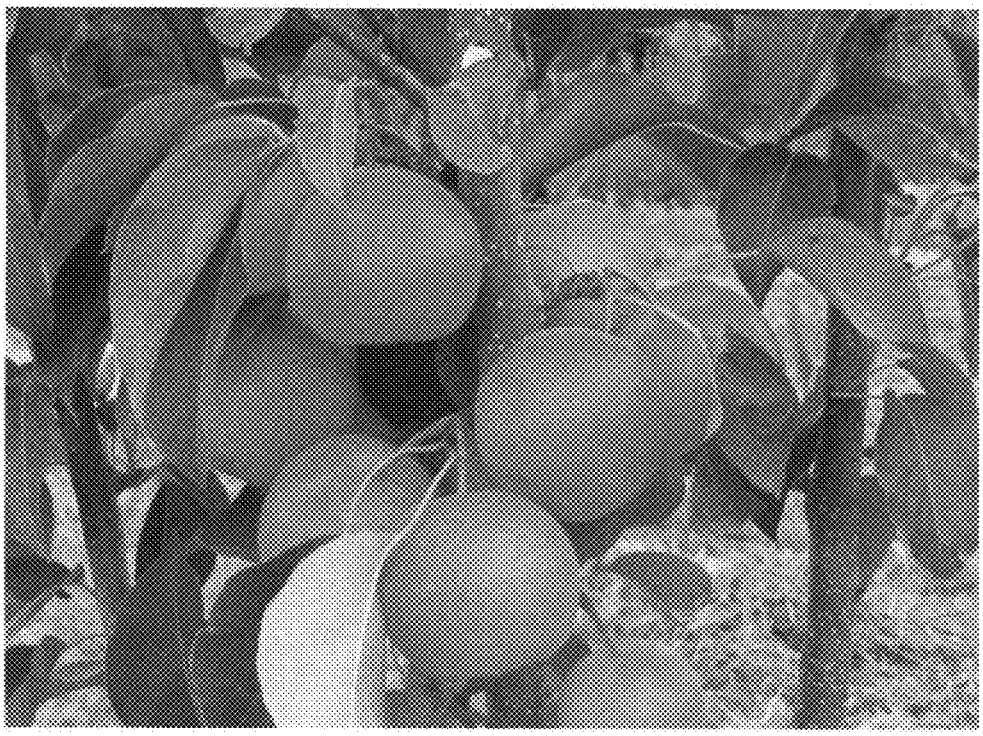
Figure 2:
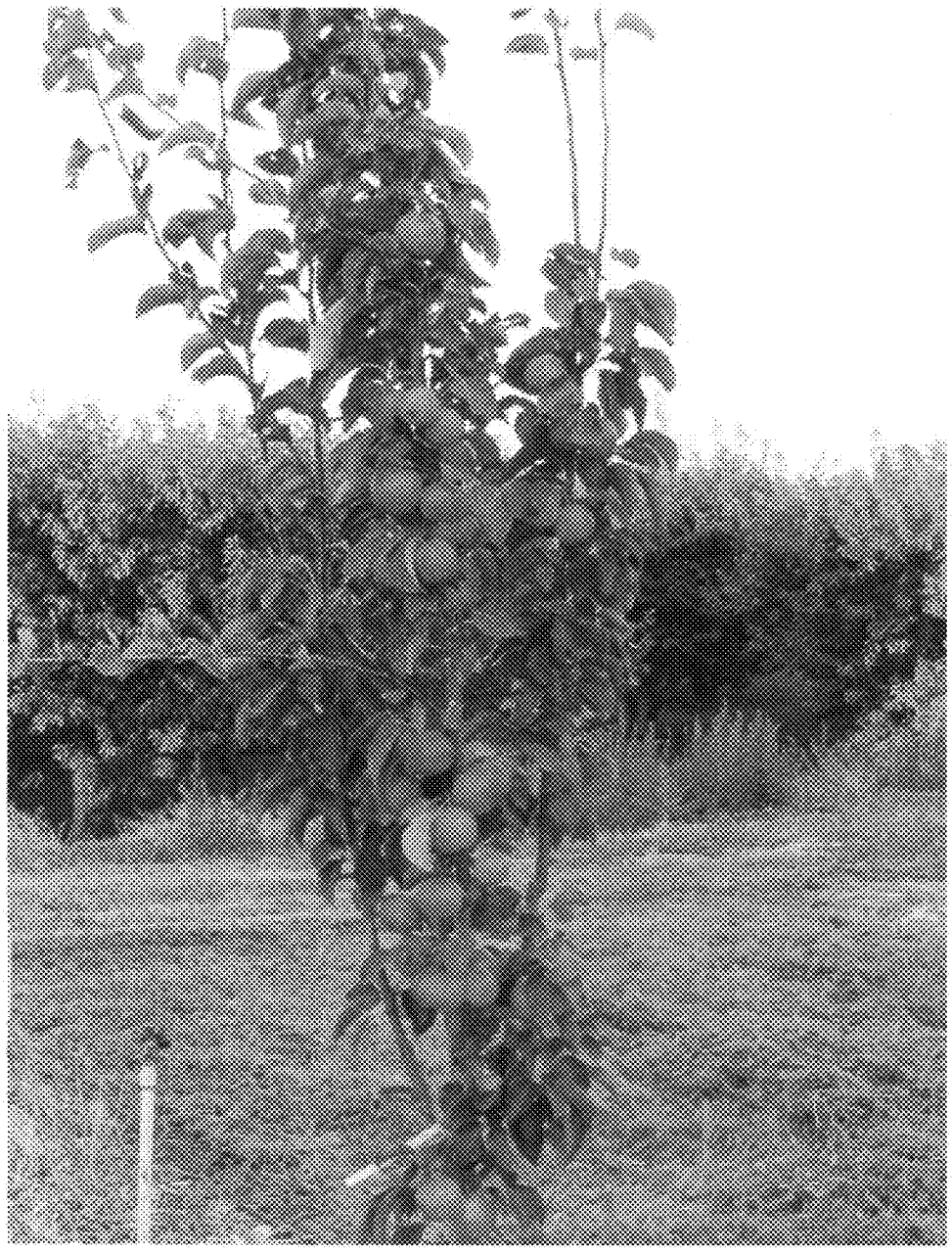

FIG. 1 shows the fruit of a 'PremP109' pear tree;
FIG. 2 shows a 'PremP109' pear tree;

BRIEF DESCRIPTION OF THE VARIETY

The new variety of pear tree 'PremP109' was created in the course of a planned breeding program carried out at Hawkes Bay, New Zealand. 'PremP109' originated as a result of a controlled cross of 'P125R74T032' (seed parent, not patented) and 'P125R95T002' (pollen parent, not patented). 'PremP109' was selected as a single plant from among a population of seedlings derived from the parents, and was selected for its attractive red color and unique appearance, superb texture and flavor, and long shelf life. PremP109 has a thinner, less bitter skin, no flesh astringency, more flavor, is larger and has no russet on the cheek compared to the parent varieties. Compared to other known Asian pear cultivars, PremP109 has a lemon color with an orange blush rather than a green color. It's larger and has more flavor with higher sugar than other Asian pear varieties. Asexual propagation by budding was first carried out in Nelson, New Zealand. The variety has since been observed over a number of asexually propagated generations, and has been found to remain true to type.

DETAILED BOTANICAL DESCRIPTION OF THE VARIETY

The following detailed botanical description is based on observations made during the 2010 growing season at Parker, Wash. on four year old trees. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Medium.
- *Habit.*—Upright.
- *Size.*—Height 213.4 cm, spread 45.7 cm.
- *Trunk.*—Diameter at 5 cm above graft union 7 cm.
- *Bark texture.*—Smooth.
- *Bark color.*—166C.

Branch:
- *Size.*—Diameter 2.5 cm at 1.37 m above graft union.
- *Crotch angle relative to trunk.*—45°.
- *Branch color.*—Over color 197D, under cover N167C.
- *Lenticel density.*—15 per square inch.
- *Winter hardiness.*—Hardy.
- *Chilling requirement.*—1,000 to 1,800 hours.

Dormant one-year old shoot:
- *Size.*—Diameter 1.5 cm, length 106.68 cm.
- *Color.*—166B.
- *Internode length.*—4-5 cm.
- *Lenticels.*—Quantity 10 per square inch, color 155B, diameter 0.5 cm.

Flowers:

*Bud*.—Quantity per spur 8-9.

*Size*.—Diameter 1 cm, length 1.5 cm.

*Color*.—65B, pink on edges.

*Petal*.—Quantity per flower 5; Touching, diameter 1.5 cm, length 2 cm, margin smooth.

*Sepals*.—Quantity per flower 5, diameter 0.2 cm, length 0.5 cm.

*Pedicel*.—Diameter 0.1 cm, length 2.5 cm, color 145A.

*Anthers*.—Quantity per flower 10, length 0.1 cm, pollen color 4C.

*Stigma*.—Size 0.1 cm, color 200D.

*Style*.—Length 0.4 cm, color 4C.

*Ovary*.—Size 0.3 cm, color 151B.

*Bloom period*.—First bloom April 5, full bloom April 10 in Parker, Wash.

*Pollination requirements*.—Yali and Hosui.

Leaf:

*Attitude in relation to shoot*.—Upward.

*Blade margin*.—Serrated.

*Shape*.—Ovate, apex acuminate, base equilateral.

*Size*.—Length 12.2 cm, width 7.2 cm.

*Color*.—Upper surface 146D.

*Color of lower surface*.—145C.

*Apex with petiole*.—2.8 cm.

*Attitude in relation to shoot*.—45°.

*Venation pattern*.—Pinnate.

*Vein color*.—144D.

*Petiole*.—Diameter 1 mm.

*Petiole color*.—144B.

Fruit:

*Size*.—Diameter 8 cm, length 6.7 cm, weight 250 g; General shape in profile round; Aperture of eye 1 cm; Size of eye 0.5 cm; Depth of eye basin 0.4 cm.

*Stalk*.—Diameter 0.3 cm, length 4 cm, color 145C; Depth of stalk cavity 0.6 cm; Width of stalk cavity 0.8 cm; Size of lenticels 0.1 cm; Ground color of skin Yellow 12C; Over color of skin Red 33B; Flesh is crisp and very juicy; Flesh color 155B; Quantity of seeds 9.

*Seed size*.—Width 0.4 cm, length 1 cm; Seed color Black 202A.

Productivity: 50 lbs of fruit per tree.

Disease susceptibility: Susceptible to Fire Blight.

Storage: Excellent storage performance of at least 10 weeks and up to 16 weeks and 14 days ambient shelf life.

Use: Fresh Market.

I claim:

1. A new and distinct pear tree substantially as shown and described herein.

* * * * *